United States Patent [19]

Mick et al.

[11] Patent Number: 5,261,404
[45] Date of Patent: Nov. 16, 1993

[54] THREE-DIMENSIONAL MAMMAL ANATOMY IMAGING SYSTEM AND METHOD

[76] Inventors: Peter R. Mick, 4 Stonybrook Trail, Kinnelon, N.J. 07405; Mark Savet, 50 Sutton Pl. South, New York, N.Y. 10022

[21] Appl. No.: 726,705

[22] Filed: Jul. 8, 1991

[51] Int. Cl.⁵ .......................... A61B 5/00; A61B 8/13
[52] U.S. Cl. ........................... 128/653.1; 364/413.13; 128/662.06; 128/660.07; 128/916
[58] Field of Search .................. 128/653.1, 653.2, 916, 128/662.05, 662.06, 660.07; 606/130; 364/413.13, 413.14, 413.22

[56] References Cited

U.S. PATENT DOCUMENTS

| | | | |
|---|---|---|---|
| 4,028,934 | 6/1977 | Sollish | 128/916 |
| 4,486,076 | 12/1984 | Taenzer | 128/916 |
| 4,791,934 | 12/1988 | Brunnett | 128/653.1 |
| 5,038,786 | 8/1991 | Kojima | 128/653.2 |
| 5,050,607 | 9/1991 | Bradley et al. | 128/653.2 |
| 5,081,992 | 1/1992 | Levin et al. | 128/653.2 |
| 5,099,846 | 3/1992 | Hardy | 128/653.1 |
| 5,146,924 | 9/1992 | Sepponen | 128/653.2 |

FOREIGN PATENT DOCUMENTS

0112582 7/1984 European Pat. Off. ......... 128/653.1

Primary Examiner—Lee S. Cohen
Assistant Examiner—K. M. Pfaffle
Attorney, Agent, or Firm—Alfred C. Hill

[57] ABSTRACT

A method and a system to provide images of the internal anatomy of a mammal wherein first images of a selected one of body cavities of the mammal are provided by externally generated tomography slice data employing existing tomography techniques, wherein second images are provided by a unique endoscope inserted into the selected one of the body cavities, and wherein the first and second images are correlated to generate composite images of the selected one of the body cavities in real time, in large fields of view and in three-dimensions. The surgeon can utilize the first images to externally select a path through the selected one of the body cavity to a surgical site. The surgeon can also select predetermined three-dimensional views from said composite images for viewing during the surgical procedure.

24 Claims, 6 Drawing Sheets

THREE-DIMENSIONAL MAMMAL ANATOMY IMAGING SYSTEM AND METHOD

BACKGROUND OF THE INVENTION

The present invention relates to endoscopic systems and methods and more particularly to an improved system and method for providing a three-dimensional (3-D) image of the anatomy of a mammal.

While the disclosed system and method has great importance in providing 3-D images of the anatomy of a human, the method and system can also be employed to obtain 3-D images of the anatomy of other mammals, such as dogs, cats, horses, fish-like mammals and the like.

Currently in the medical profession there are significant numbers of surgical procedures which involve the use of microsurgical instruments and imaging systems. These allow procedures to be performed via trocars avoiding the need for open surgery, such as laproscopic cholecystectomy, etc.

A significant problem associated with this type of procedure is the limited ability to visualize or see the anatomy which is being traversed by the instrumentation. There is also the problem of obtaining views of the anatomy at the surgical site which are clear and meaningful, in the light of the procedure being attempted. Hence, the number of surgeons attempting these new procedures are limited as are the number of anatomic sites where they are presently employed.

Generally an imaging system consisting of an optics head disposed in a trocar which is inserted through an incision in the wall of a body cavity. This allows a view of the anatomy to be observed by the surgeon, dependent on the field of view of the optics. The image from the optics head can be relayed via a coherent fiber optic bundle, or a solid state imager at the image plane. The resulting image can be displayed to the surgeon via an eyepiece, such as a set of goggles, or on a CRT monitor which can be located close by.

Under current technology the view the surgeon sees is that provided by the optics head which has some limitations, for example, VIEWPOINT—Frequently, instruments are placed through the same trocar as is the optics head yielding a view of the anatomy which is partially blocked by the instruments. It should be noted that the viewpoint determines the anatomy observed by the surgeon. If the field of view is small there are fewer landmarks to recognize the general location of the instrument and optical head within the anatomy. If the field of view is large then detail is lost.

DEPTH PERCEPTION—As the instruments in the same trocar as the optics head are moved further from the optics head, the perception of where the instruments are located becomes confusing, relative to the target anatomy.

DEPTH OF FIELD—As the anatomy is viewed through the optics head, a fixed depth of field exists, that is, objects in front of and behind the viewed anatomy, are out of focus. This causes the surgeon to lose information relating to potential hazards as well as landmarks.

The need clearly exists to improve the quality of imaging for minimally invasive surgery.

SUMMARY OF THE INVENTION

An object of the present invention is to provide an improved 3-D mammal anatomy imaging system and method.

Other objects of the present invention include fully focussed images, multiple viewpoints from a stationary optics head, 3-D images, images resulting from connecting multiple high resolution images together in 3-D to provide a panorama of the anatomy not currently available, the ability to traverse the anatomy prior to penetrating it with instruments to establish the optimum route therethrough, and the possibility of performing surgery remotely, that is, over wideband information channels, such as telephone, fiberoptic cables, microwaves, etc., whereby a surgeon at a remote location, could through local manipulators and a 3-D monitoring device be allowed to select views remotely, thus, allowing skilled surgeons to perform operations from a remote location on patients located in different parts of the world.

A feature of the present invention is the provision of a method of providing images of the internal anatomy of a mammal comprising the steps of providing from externally generated tomographic slice data provided by existing tomographic techniques first images of a selected one of body cavities of the mammal; producing from within the selected one of the body cavities second images thereof; and correlating the first and second images to generate composite images of the selected one of the body cavities in real time, in large fields of view and in 3-D.

Another feature of the present invention is the provision of a system to provide images of the internal anatomy of a mammal comprising first means to externally generate tomographic slice data by existing tomographic techniques to provide first images of a selected one of body cavities of the mammal; second means to produce from within the selected one of the body cavities second images thereof; and third means coupled to the first and second means to correlate the first and second images to generate composite images of the selected one of the body cavities in real time, in large fields of view and in 3-D.

BRIEF DESCRIPTION OF THE DRAWING

Above-mentioned and other features and objects of this invention will become more apparent by reference to the following description taken in conjunction with the accompanying drawing, in which.

DESCRIPTION OF THE PREFERRED EMBODIMENTS

A method and system is disclosed which allows the internal anatomy of a mammal to be imaged in real time, in large fields of view, and in three dimensions. It further allows a surgeon, operating through a trocar, to precisely know where his instruments and imaging viewpoint are positioned in the general anatomy. Additionally, it allows the surgeon to select a view of the anatomy which shows the present location in the anatomy as well as the target anatomy which he is seeking.

The system and method further allows him prior to actually inserting instruments into the body cavity to select and traverse the path or course selected in order to avoid high risk regions or structures which may be interposed between his present location and the target surgical site.

When the surgeon visually traverses the path to the target anatomy he does not need to move the endoscope or other instruments. This is accomplished by voice commands or a joystick control of the image processor such that his eye position is advanced in three dimensional space. Thus, the surgeon, in an external position can observe the anatomy from an internal viewpoint at a location he selects and controls. The viewpoint selected simulates the scene the surgeon would see if he was at that location, that is, with full three dimensional views, which are fully focused in all three dimensions. In addition, he has controllable degrees of perspective, magnification, orientation relative to the plane of his eyes, and the viewing field can be centered anywhere in the $4\pi$ steradians of the viewing location.

Hence, the surgeon is permitted to "walk through" various paths to the target anatomy and select the one with the greatest surgical impact. Once selected, he introduces the attendant instrumentation into the body cavity and along this path to the site of the surgery, or selects multiple paths for the instruments, set up at different external location on the patient. Having reached the site of surgery the surgeon can exercise the same degree of freedom in observing the local anatomy which he employed to determine the path to it.

It should be noted that the techniques being presented would be clearly applicable to telescopes and microscopes, both two dimensional and three dimensional.

The invention embodies the use of existing high resolution imaging (that is, Orthogonal X-RAY, CAT SCAN, NMRI, and PET, etc.), as well as images taken in essentially real time through a unique endoscopic optics head as disclosed herein. If conventional support imaging is not available the present invention provides its own image processing system.

The existing high resolution imaging referred to above is tomographic in nature which employs the collection of data representing cross sections of a body. A plurality of object interrogations can be processed mathematically to produce representations of contiguous cross-sectional images referred to herein as slice data. Such cross-sectional images or slice data are of great value to the medical diagnostician in a non-invasive investigation of internal body structure. The techniques employed to collect the slice data can be, for example, X-ray computed tomography, nuclear magnetic resonance (NMRI) tomography, magnetic resonance (MRI) tomography, singlephoton emission tomography (SPET), positron emission tomography (PET), ultrasound tomography and CAT-SCAN tomography.

A three dimensional memory containing the image of the anatomy of a patient is developed through the use of image processing techniques for the region of interest. This volumetric image is further processed allowing the surgeon to obtain views, i.e. cutting planes and surfaces which optimally services his needs.

The volumetric image is generated from images obtained from the above-mentioned existing tomographic techniques which have been "pieced together" to form a continuous volume, calibrated dimensionally in three dimensions.

The present invention comprises four major elements: (1) generation of 3-D volumetric image information; (2) formation of three dimensional images of the anatomy of interest stored in memory; (3) selecting images (two or three dimensions) which provide the required information for the surgeon, that is, a close-up view of the anatomy, oriented optimally for surgery, or a broad view showing the relative positions of the anatomical structures, allowing the surgeon to orientate himself exactly relative to his present position, and the choices of paths he has to the target anatomy; and (4) three dimensional display of information to the surgeon and his or her assistants.

Images employed to generate the three dimensional volumetric image come from two general areas;

(1) EXISTING IMAGING TECHNIQUES as mentioned hereinabove. These provide a series of "slices" which can be further processed by existing conventional methods to provide three dimensional data relating to a specific patient's anatomy. This data would be stored in a conventional three dimensional image array memory, and have resolutions comparable to the resolution of the scanner. Additionally, this image data can be enhanced by conventional image processing and coloration techniques prior to storage. Through the use of radio opaque photon sensitive, or magnetic resonance in the case of PET and NMRI, respectively) tape fixed to known locations on the body, the exact location of the imagery can be referenced to the body surface (longitudinally and circumferentially). The tape can be coded in binary (in the radio opaque medium) in a nonambiguous code which allows its location in the image or slice to be precisely related to the body surface location.

(2) THREE DIMENSIONING ENDOSCOPE. A critical element of this invention is an endoscope which has the ability to image a body cavity in three dimensions. The system employs a solid state imager to pick up the image generated by the optics head. The imager may be at the image plane of the optics head or pick up the image from a fiberoptic bundle face which transmits the image from the image of the optics head through a trocar.

The optics head is designed such that changes in axial spacing of the multiple lenses and image plane, change the location of the "focus surface" of the optics. By changing these relative spacings the region of focus can be moved from the near field of the body cavity to the far field of the body cavity. The axial dimension of the depth of field being controlled by lens design, aperture size, focal length, etc.

The lenses are driven mechanically through the positions which cause the focused surface to move through the body cavity. The rate at which the focused surface moves through the cavity is such that images can be captured at rates which are compatible with conventional imagers (more than one hundred scans/sec.). At the same time they utilize a short axial depth of field. During this scanning process the optical acceptance angle remains constant.

Objects within the body cavity are at different distances from the optics. The focused surface through the body cavity is generally not flat, although generally radially symmetric, therefore, different pixels or points come into focus as a function of both their distance from the optical axis, as well as the relative spacing of the lenses. The distance to a pixel which is in focus is known from its x, y location on the imager, the relative spacing of the lenses when they come into focus, and the shape of the focused surface for that lens spacing. When an in focus pixel is detected it is stored in a three dimensional memory at the x, y and depth d location it was detected.

As the memory is filled a surface is generated within it that is an in focus image of the body cavity. The number of pixels entered into the memory is equal to the size of the imaging array, for instance, 256×256, 512×512, etc, since each element (pixel) of the array only comes into focus once, at the focus depth, throughout the cavity.

This stored three dimensional surface represents an image taken with a lens system of known characteristics. The lens system is entered into the body at a known location on the body surface, and at known angles. Hence, the location of all elements in the image can be related to absolute locations within the body.

By removing the camera's perspective from the stored image, by conventional trigonometric means, the stored image should closely correlate with the actual anatomy of the patient, and a region of an image taken by other means such as the above-mentioned existing tomographic techniques.

Once the image from the optics head is stored in memory the optics head can be physically moved to a new location within the body with several degrees of freedom namely, x, y, z locations of the optics head, pointing angle of the optics head (azimuth, declination), rotation of the optics head (0-360 degrees) and acceptance angle of the optics head.

At this new location another three dimensional image can be generated which overlaps or borders on previously stored images. This allows a much larger image to be generated by the optics head than would be taken with a single "snapshot".

The matching of the multiple images is achieved by two means; (1) image processing (correlation); and (2) computing image elements from known camera movements.

Two types of images in three dimensions exist prior to the formation of a composite image derived from the two. One from the endoscopic optics head of the present invention within the body cavity, the other from processed "slice images or data" derived from existing tomographic techniques. The images from the optics head are "decalibrated" (perspective removed) and scaled geometrically to the images from the "slice" data.

The procedure for correlating the optics head image with the "slice" image requires that standard image processing techniques be employed to reduce the amount of data in each memory temporarily to facilitate the correlation.

Techniques such as gradient searches, sobel transforms and edge enhancement, allow both images to be reduced in the region of interest, to a simpler form, i.e. binary images of structure edges.

Due to insufflation the optics head image has a certain degree of distortion associated with it. This is primarily in terms of depth, and in terms of the spacial frequency content of the image, and presents a very low frequency component. This, when considered, does not materially impact the correlation of the two images. When the images are correlated, the portion of the region of interest from the "slice" images is added to the optics head image. This provides detail to the region of interest not immediately visible to the optics head. This allows all the objects behind those structures which block the view of the optics head to be added to the region of interest.

As the position of the optics head is changed the correlation process is repeated. The region of interest contains all information from the optics head image, and only uses the "slice" data to fill the regions not visible to the optics head. The optics head information, present and past, is always used in the region of interest because, (1) it is "live" (real time), and represents the most recent location of the structures, (2) it accurately depicts the sufflation-induced geometrical distortions, (3) it accurately represents anatomical coloration, (4) it shows the present position of the instrumentation in the region, and (5) it shows changes in anatomy resulting from surgery.

Once the volume representing the region of interest has been specified by the surgeon and entered into memory the surgeon has complete control of the view selection.

If the region of interest is thought of as a box containing objects, or anatomical structures, some of the options the surgeon has for selecting the image he sees are; (1) images created by cutting planes through the volume, (2) images created by surfaces cutting through the volume, (3) isolated structures/organs viewed from any location on a surrounding sphere ($4\pi$ steradians) at different radii (perspective), (4) views from a point inside the box looking outwardly in a direction of any azimuth and elevation through varying viewing angles, and (5) views from outside or inside the box which allows intervening structures between the viewer and remote objects from the viewing point to become partially or totally transparent, that is, considerable edge definition but large interconnecting surfaces of low spacial frequencies, transparent or color tinted. The surgeon also has the ability to provide selective optical magnification to; (1) regions of the object that is being imaged, and (2) portions of the solid viewing angle.

In the region of each of the viewing points the surgeon can establish two viewing points on a straight line through the initial viewing point. Each of the viewing points is located an equal distance from the original viewing point. The separation between the two viewing locations is variable, and the viewing direction of each of the new viewpoints is at a common vanishing point. This is located on a line through the initial viewing point and in the direction of the initial viewing direction, and perpendicular to the line connecting the two new viewing points. The distance of the vanishing point along this line is variable. The line connecting the two new view points can be rotated through 360 degrees in a plane perpendicular to the line containing the vanishing point, that is, two new viewing points representing the location of the surgeon's eye for stereoscopic viewing.

The images generated for each of the two viewpoints can be separately stored or generated in essentially real time for display from the common "region of interest" memory.

The image manipulation techniques reviewed already exist in present CAT SCAN image analysis techniques as well as in the JPL Image Processing Laboratories (IPL), Library of Image Processing Technology.

Image selection is critical to the surgeon. It has to be rapid, precise, and easy to implement. There are several methods for image selection and control. One, for example, can be made to operate on voice commands. A series of simple commands are used to locate the viewpoint location, that is, locate up, locate down, locate left, locate right, locate in, locate out, etc. The angular position of the viewpoint would be adjusted with simple commands, that is, left, right, up, down, etc. Zoom in and zoom out, similarly, would be voice commands.

Insufflation in the "slice" imagery can be simulated with image processing techniques. A point of inflation can be selected and regions or boundaries surrounding this point can through image processing techniques allow a "gas bubble" to be initiated at this point. The bubble grows with increasing simulated pressure. The actual movement of the adjacent structures under real insufflation can be used to model the simulation in imagery.

Prior to an actual procedure the surgeon would have the ability to simulate the procedure using slice imagery. He could, by voice command, select the location of entry on the epidermis, effect an entry, and have a view point in three dimensions within the anatomy. By simulated insufflation, inflate the region, look around it and move through it, selecting, evaluating, and investigating pathways and interviewing structures on the way to the target anatomy. Once at the site of surgery he would be able to view, from essentially any vantage point, the surgical field in three dimensions. Since the slice imagery contains all internal structures he would be able to enter organs, aortas, etc., with his viewpoint positioning capability. The physical entry to the body is initiated once the "simulated surgery" has been completed and the strategy for a particular patient has evolved in terms of the optimum pathways and procedures.

A trocar or similar device is entered into the body, and the optical imaging system and insufflation equipment is entered through it, and the angle and depth of the optics head is continually tracked.

Once the image is formed by information from the optics head it is in the "optics" memory (a three dimensional surface in which the camera's perspective has been removed). The image processor, using three dimensional correlation techniques, fills in the regions of the optics memory which were incomplete due to the viewpoint of the camera. The complete regions resulting from the structures are interposed between the camera and the rear surfaces of the insufflated cavity.

The surgeon can cause his viewpoint to be moved at will through the cavity using data received from the optics head, or move through a surface boundary where the imagery would be slice information.

As the surgeon moves the optics head, new images are taken and processed as described above, and the three dimensional memory is expanding allowing the different views from the optics head to be connected, in three dimensions, through the use of correlation techniques. The views from the optics head will frequently contain images of the instrumentation required for the procedure. These images would have to be removed by standard image processing techniques from all views, except the most recent in time.

A preferred display method of three dimensional goggles or helmets allow the surgeon to be "immersed" in the anatomy, allowing him to move through the regions of interest at will.

The left eye is presented with an image from the left eye view point memory and the right eye an image from the right eye view point memory. The three dimensional information is resident in the computed contents of the viewpoint memories and the image projection into the respective eye allows the psychovisual system to perceive the memory contents as a three dimensional image such as in sterographic imaging.

Color information, stored in terms or red, green, blue (RGB) video, or high resolution digitized composite color video, would be provided to a display device for each eye such as;

(1) miniature color CRT's with compatible optics to the eye, focused by the user, driven with RGB or composite video, and (2) flying spot scanner using three color optics, such as appropriately filtered white light or laser light.

Information provided to the goggles can also be displayed on CRT type monitors, collapsing the depth dimension along the viewing optical axis. These additional displays would facilitate the assistants and nurses in their support during the surgical procedure. The surgeon's goggles will have the ability, under voice command control, to remove the image of the anatomy and present a view through a transparent window to the outside world. This function could be implemented by methods such as a mechanical shutter, or electrically-operated shutter, used as a liquid crystal display.

It is not intended to limit the scope of application of this invention to surgical procedures. For example, the imaging system of the endoscope described could characterize volumes of translucent or semi-transparent particulates in regions by their back scattering, or transmission characteristics such as might be found in the posterior eye (vitrious gel) or cataracts in eyes. Hence, the volumetric image would quantify the degree of degradation within the lens and anterior chamber. This volumetric image quantifies to the optical transmission characteristics of the anterior eye. This type of information provides a reference for measuring subsequent deterioration through ripening. Hence, surgeons can have an opportunity to characterize the problem in terms of time and degree.

Similarly, in the assembly of micro-miniature machinery or devices variable viewpoints are necessary to perceive the special relationships involved, in order to maintain the high precision and required accuracy, as in surgery. This equally applies to all such products which may be manually or automatically produced and/or assembled.

The technology being presented uses broadband visable light as the propagating energy that is controlled, measured, and displayed.

Clearly, narrower and broader portions of the electromagnetic spectrum can be employed to achieve a three dimensional image. For example, very narrow band laser illumination from the far infra red to the far ultra violet. Also X-rays and RF energy from very low frequencies through microwaves can be used. Each energy source being used for illumination requires appropriate lenses for the particular frequencies being employed, and sensors compatible with the spectrum being imaged i.e. for IR, germanium lenses and pyroelectric sensors. Similar considertions would make sonic and ultra sonic imaging practical using existing technology (medical and seismic) to one skilled in the art.

The source of illumination does not need to be restricted to types that "flood" the area to be imaged, but instead can be of a scanning nature, whereby the illuminating beam of energy is approximately the same resolution as the imager and scans synchronously with the scanning of the imager, affording energy conservation in illumination as well as minimization of reflected illumination from objects in the scene not being directly illuminated by the beam.

Although the embodiment described employs reflected energy, it is clear that illumination can be provided by transmitted energy, such as used in present day X-ray equipment, without modifying the spirit of the invention.

The novelty of the present invention resides in two general areas; (1) employing and combining existing or conventional "slice" type imagery with surface imagery generated with a unique endoscopic system, and allowing a surgeon the ability to visualize the anatomy of interest from varying viewpoints and perspectives in three dimensions, and (2) the design of the endoscopic system to provide the surface imagery required for the above system.

The previous descriptions provide the methods of combining volume and surface images and allowing view points to be located throughout the surface/-volume region of the anatomy of interest. To one skilled in the art, the prior descriptions of the image generations and display, combined with well known techniques to manipulate images, would allow such a system to be constructed if the surface imagery was available.

The following paragraphs described the detailed generation of the surface imagery.

The objective of the moving optics disposed inside or outside the body is to provide optical information to a solid state imager, such as a CCD or CID array, which, when processed by the image processing circuitry, will provide surface information to a memory. This memory is representative of the region in the field of view of the optics acceptance angle. The information when entered into the volumetric surface memory will be in focus throughout the entire depth of the cavity being viewed. Each focused pixel point will be located in the memory at a depth proportional to the depth of the actual object in the field of view (FOV).

Figures 1, 2:
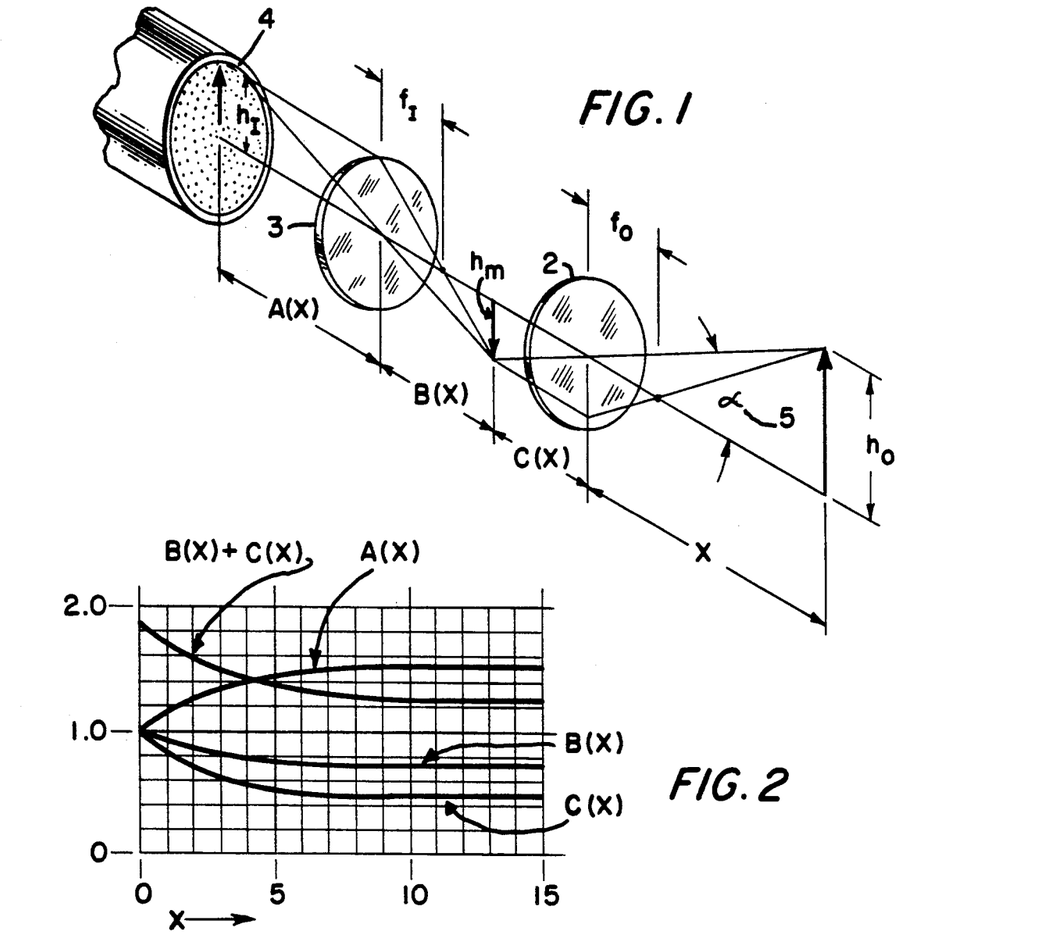
FIG. 1 is a perspective view of a representation of one embodiment of an optics head employed in the imaging system in accordance with the principles of the present invention.
FIG. 2 is a graph illustrating the displacement of the lenses of FIG. 1 as a function of the object distance useful in explaining the operation of the optics head of FIG. 1.

In order to achieve this objective a plurality of lenses, that is, two or three are mounted on a common optical axis 1 as shown in FIG. 1. As shown in FIG. 1 two lenses 2 and 3 are disposed in tandem along and perpendicular to optical axis 1.

The spacing between the image surface 4 and image lens 3, $A(x)$, the spacing between image lens 3 and the object lens 2; $B(x)+C(x)$, and the focus distance x of the object $h_o$ is variable. The acceptance angle $\alpha$, 5, is approximately constant, independent of the focus distance x of the object from the object lens 2. An object "filling" the field of view, independent of its distance, x, will cause the object to be imaged on the image surface 4 at a constant size, $h_I$. As the lenses 2 and 3 move relative to each other and the image surface 4, the focused surface, the region in space in front of the optics which causes an object to create a focused image, moves through the entire cavity being imaged.

An object at a distance x from the object lens 2, will form an inverted image between the object lens 2 and the image lens 3 at a distance $$C(x) = \frac{xf_0}{x - f_0}$$

where $f_o$ = focal length of object lens 2

Since an object $h_o$ fills the FOV at a distance x will create an intermediate focused image ($h_m$) at a distance $C(x)$ behind the object lens 2, $$\therefore \frac{h_0}{x} = \frac{h_m}{C(x)} = TAN\alpha = constant$$

This intermediate image ($h_m$) is imaged by the image lens 3, with a focal length $f_I$. The intermediate image ($h_m$) becoming the object for the image lens 3. The image plane or surface of the image lens 3 is the fiberoptic bundle or solid state imager 4. The image height ($h_I$) being constant for an object which fills the FOV of the object lens, i.e. $$A(x) = \frac{f_I B(x)}{f_I - B(x)}$$

and $$h_I = \frac{A(x)}{B(x)} h_m = constant$$

FIG. 1 shows the geometry just described and the following indicates the mathematics governing the various relationships involved.

$\alpha$ = constant; $h_I$ = constant; x = distance to object $h_o$ surface $A(x)$, $B(x)$, $C(x)$ are adjusted to cause object surface to be in focus $$\alpha = TAN^{-1} \frac{h_0}{x} ; \frac{1}{f_0} = \frac{1}{x} + \frac{1}{C(x)}$$

$$\frac{h_0}{x} = TAN\alpha = \frac{h_m}{C(x)} ; \frac{1}{f_I} = \frac{1}{A(x)} + \frac{1}{B(X)}$$

-continued $$\frac{h_I}{A(x)} = \frac{h_m}{B(x)}.$$

By employing algebra the following relationships defining $A(x)$, $B(x)$ and $C(x)$ are obtained.

$$A(x) = f_I\left(1 + \frac{h_I(x - f_0)}{xf_0 \text{TAN}\alpha}\right)$$

$$B(x) = \frac{f_I(A(x))}{A(x) - f_I}$$

$$C(x) + \frac{xf_0}{x - f_0}$$

FIG. 2 is a graph showing the displacements $A(x)$, $B(x)+C(x)$ as a function of $x$ in normalized units, with the following exemplary values $\alpha=45°$, $f_0=\frac{1}{2}$, $f_I=\frac{1}{2}$, $h_I=1$.

It can be noted that a slight variation, for the focal lengths selected, in the displacement of the object lens 2 occurs relative to the image plane 4. The sum of the two curves $B(x)+C(x)$ and $A(x)=1,2$ units. The third lens would eliminate this displacement.

Figure 3:
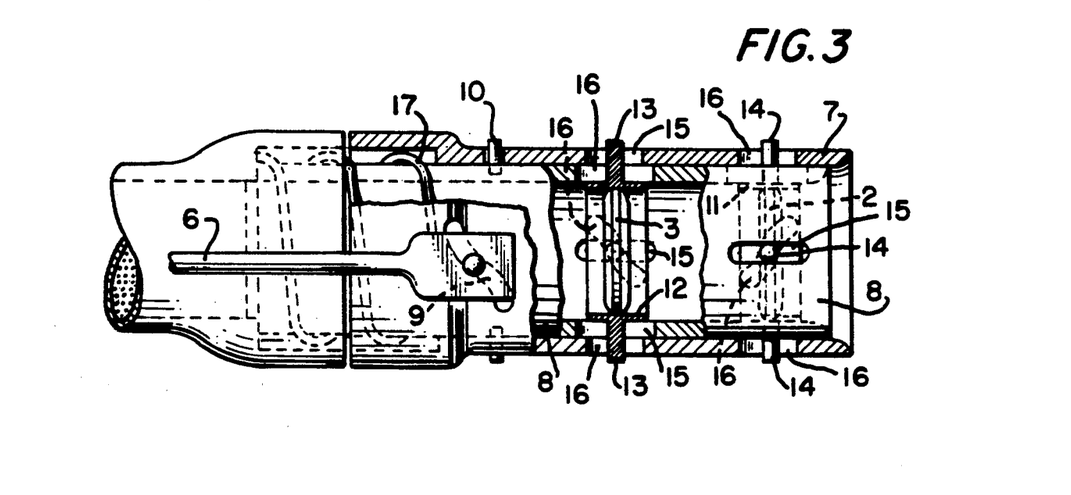
FIG. 3 is a cross-sectional view of one possible implementation of the optics head of FIG. 1.
Figures 4, 5, 6:
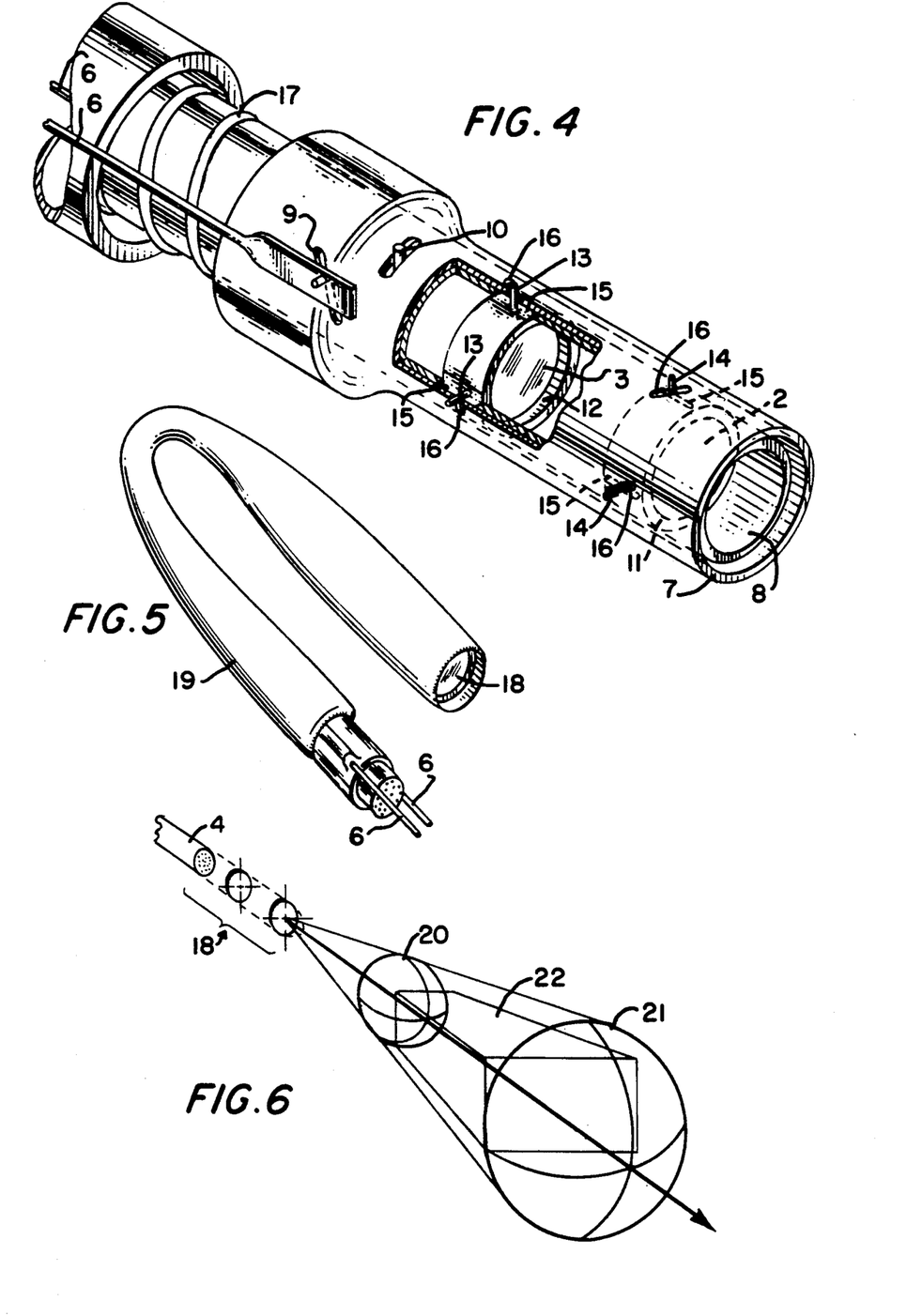
FIG. 4 is a perspective view of the implementation of the optics head of FIG. 3.
FIG. 5 is a perspective view of an endoscope employing the optics head of FIGS. 1, 3, and 4.
FIG. 6 is a perspective view illustrating the movement of the in focus surface as the lenses of FIGS. 1, 3, and 4 are moved.

FIG. 3 is a cross-sectional view and FIG. 4 is a perspective view of one implementation of the optics head of FIG. 1. A linear motion of motor driven pulling cables 6 causes the lenses 2 and 3 to move in the manner illustrated in FIG. 2. Cables 6 can be driven hydraulically, by a solenoid or by a piezoelectric device.

As the cables 6 are pulled, outer cylinder 7 tends to rotate relative to inner cylinder 8. The degree of rotation of cylinder 7 per unit of linear displacement of cables 6 is controlled by the curvature of slot 9. Inner cylinder 8 cannot rotate or be displaced linearly due to pin 10.

The two lenses 2 and 3 are mounted in cylindrical bands 11 and 12, respectively, which fit inside inner cylinder 8 and have four pins 13 and 14 to position each of them relative to the outer cylinder 7. Four slots 15 on inner cylinder 8 are aligned in a direction parallel to the optical axis for each lens. Four non-linear slots 16 on outer cylinder 7 allow the pins 13 and 14 of each lens 2 and 3 to pass through them from linear slots 15 on inner cylinder 8.

As outer cylinder 7 rotates due to the displacement of cables 6, the two lenses 2 and 3 within inner cylinder 8 move along the optical axis with the displacements of each, independent of the other. Their displacement is controlled by the shape of non-linear slots 16. This allows the equations of displacement $A(x)$, $B(x)$ and $C(x)$ above to be implemented.

If the cables 6 are only used in tension, outer cylinder 7 can be returned to its initial displacement by a restoring spring 17. The above method description is only intended to describe one possible means of displacing the lenses.

Alternative methods would be obvious to those skilled in the art which could consist of linear or rotational actuators, employing electrical solenoids, hydraulic/pneumatic, or piezoelectric devices. Critical to the method is the ability to known exactly what the locations of the lenses are along the optical axis at all times. To achieve the necessary accuracy, additional measures, that is, a linear encoder could be employed to ensure the necessary accuracy. Two important methods of displacing the lenses are considered, and both can be implemented with the previously described methods.

The lenses 2 and 3 can move in an oscillatory fashion as described with respect to FIGS. 3 and 4 whereby the first half cycle of translation is reversed for the second half cycle. The other method is to have the lenses 2 and 3 traverse the first half cycle of displacement then "fly back" to their original positions, in a small fraction of the time of the initial half of displacement.

FIG. 5 depicts the optics head 18 covered in a smooth protective covering 19 allowing its entry into a body cavity.

If a fiber optic bundle is used to transport the image from the image plane, that same path can be used to provide the necessary illumination in the body cavity. A conventional beam splitter introduced into the bundle would allow the light to propagate through the bundle and optics head to the anatomy while allowing the image to traverse the reverse path.

One of the principal objectives of the invention is to be able to translate a "surface" through a body cavity which is in focus.

FIG. 6 illustrates the movement of the in focus surface employing the optics head 18 of FIGS. 1, 3 and 4. The optics head 18 provides the relative positions of lenses 2 and 3 and image plane 4 initially to create a surface in the near field of view which is in focus as shown at 20. The nature of the optics head 18 determines the shape to the surface 20 and its depth of field.

The depth of field is determined by the design of the optics head, with emphasis on making the depth of field very small, that is, relative to the depth that the focused surface will traverse in the body cavity. Hence, a high degree of depth resolution is provided. As the lenses 2 and 3 move continuously, the near field surface 20 moves to the far field focused surface 21 sweeping the focused surface through the body cavity. This process repeats continuously.

A region between the near field 20 and the far field 21 is called the "imaged volume" 22 in which the location of all focused points are stored with each location being identified by the horizontal (H), vertical (V) and depth (d) values $(H,V,d=f(H,V,SN)$. This is rectangular in shape to accommodate conventional solid state memories (RAM). The vertical height of the volume is the same as the number of vertical elements (V) of the imager. The horizontal width is the same as the number of horizontal elements (H) in the imager.

The depth d is calibrated in terms of "scene number", SN, which is approximately the "depth of field" or focus width divided into the depth of the imaged body cavity, that is, 0–127, 0–255, etc.

Figure 7:
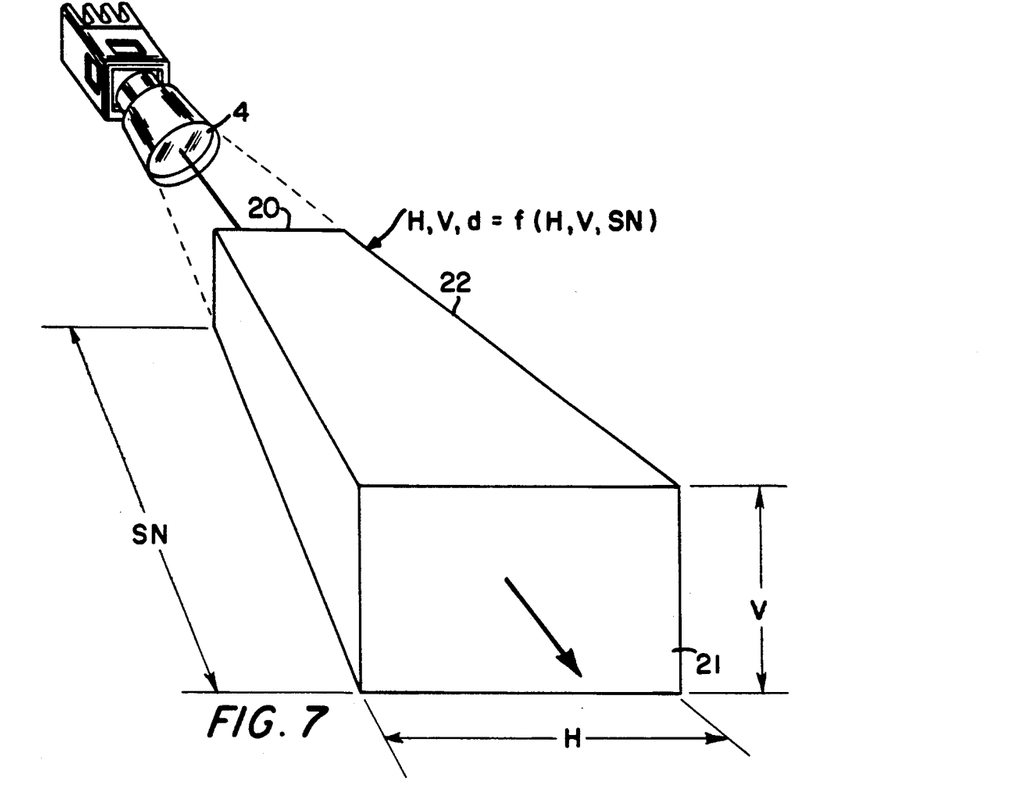
FIG. 7 is a graphical representation of the imaged volume as derived by movement of the lenses of FIGS. 1, 3 and 4.

The imaged volume referred to above is illustrated in FIG. 7. The number of volume elements (voxels) in the imaged volume can contain is $(V \times H \times SN)$. For example, if the resolution in all three dimensions was 256, the number of voxels would be 16, 777, 216. It should be noted that the "volume" of each element is not constant, due to the perspective of the optics head, that is, axis voxels in the near field 20 are considerable smaller than elements in the far field 21.

For each SN there is an area (horizontal and vertical) which represents the location of all the pixels of the array. For each pixel there is a "scene" SN where the pixel comes into focus. This occurs at a depth where the "object" is something that a particular pixel "sees" or encounters.

It is the objective of the electronics to determine the depth for each array pixel, that the object of that pixel comes into focus. Once this depth is determined then that pixel is (gray scale or color) loaded into the memory at the V, H, and depth location of focus. When focus is detected its coordinate H, V, SN and Gray scale are stored in the focused video memory.

Figure 8:
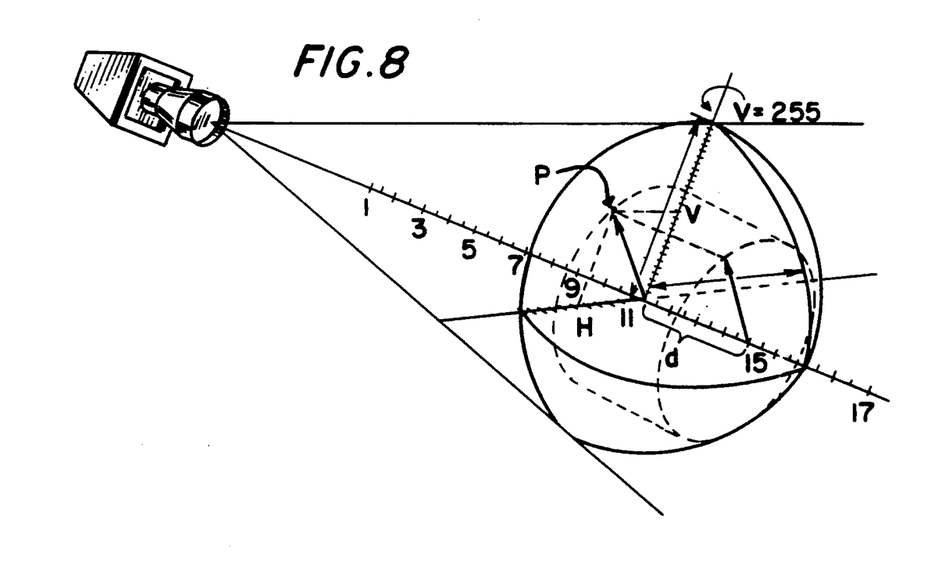
FIG. 8 is a graphical representation of how depth of an image is determined when the optics head of FIGS. 1, 3 and 4 is employed.

When the process is complete the memory contains a "surface" that is the image of the body cavity, with each focused pixel occupying a voxel related to its actual location within the body cavity. Due to the fact that the focused surface is not flat, when a pixel P comes into focus, it is not necessarily at the "SN" depth that focus has occurred. FIG. 8 illustrates a typical situation where a pixel comes into focus which is located at a particular H and V location and the lenses' relative position indicate a particular SN (SN=11 in FIG. 8). The correction can be accomplished as follows assuming the following measured coordinate data: H=0→511 (9 bits); V=0→511 (9 bits) SN=0→60 (6 bits) and GS=0→255 (8 bits), where GS=Gray Scale. The radial distance $R=[(H-255)^2+(V-255)^2]^{\frac{1}{2}}$. By employing a look up table, enter the table at the measured value of SN and calculated value of R and obtain the value of SN+d.

Since the surface will have radial symmetry, it can be generated by a curved line rotated about the optical axis. The nature of this line can be computed from the characteristics of the optics head from simple experiments. If the side of the focus surface nearest the optics head (widest opening) is considered to be at the SN location, the actual depth of the pixel in focus can readily be calculated. This can be accomplished by calculating the radial distance R of the pixel from the optical axis and entering a lookup table at "R" which contains the "line" of the focus surface and readout ΔSN. The value is determined for the actual depth as ΔSN+SN.

Due to the nature of the optics the curved line used to generate the surface of revolution may vary as a function of SN requiring a lookup table with a dual entry, that is, SN and R.

Figure 9:
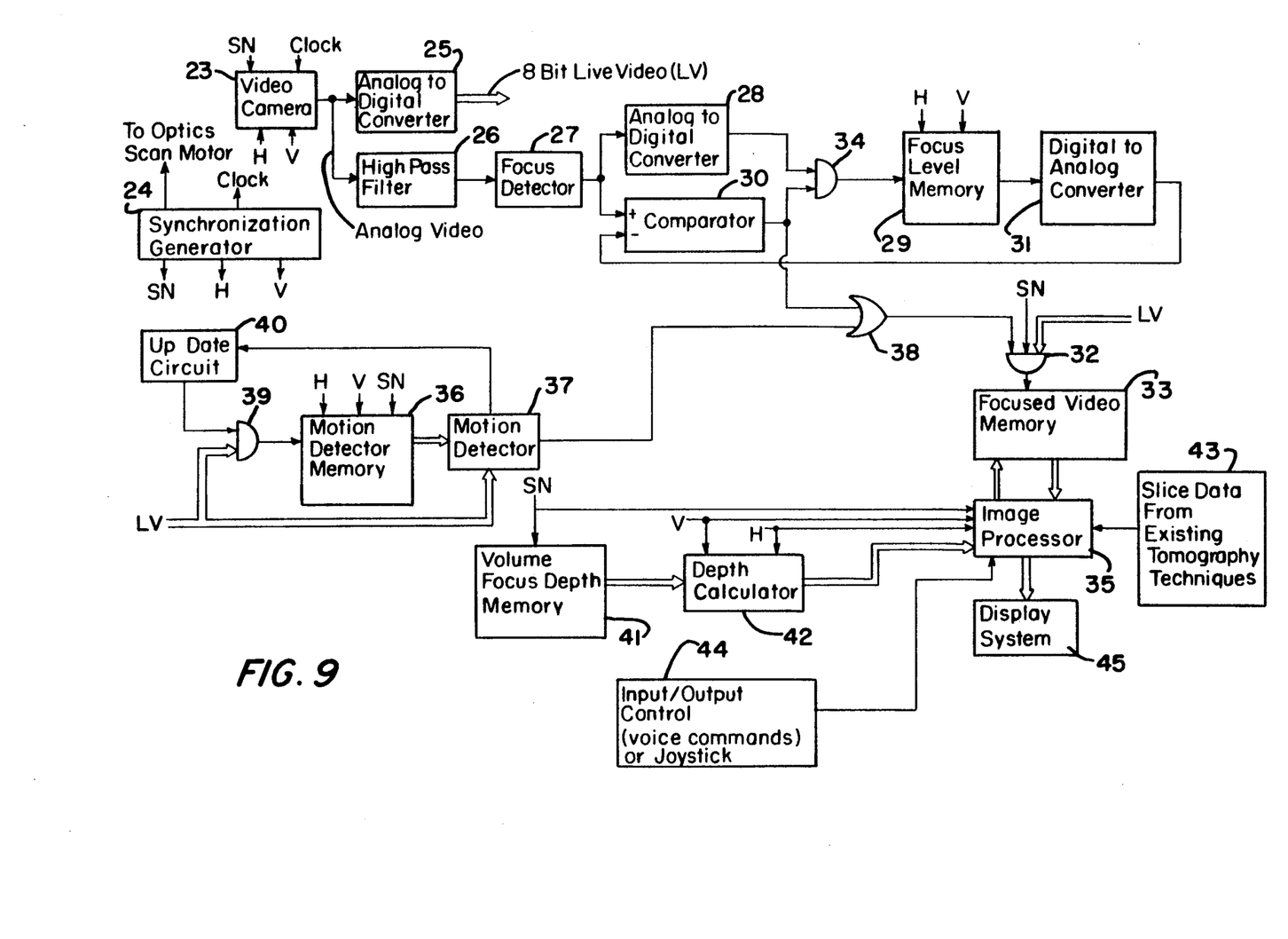
FIG. 9 is a block diagram of a 3-D mammal anatomy imaging system in accordance with the principles of the present invention.

FIG. 9 is a block diagram of a system in accordance with the principles of the present invention to capture the focused surface and provide a display. FIG. 9 represents an embodiment which would be commercially feasible, although it does not represent the embodiments which provide the highest degree of performance. The input to the electronics is video from a camera 23 which is scanning in conventional television formats, or in a format designed specifically to optimize performance of the system.

A synchronization generator 24 provides signals H, V, SN and clock for camera 23 and also signals to the optics head for scanning the lenses 2 and 3. Generator 24 also provides all synchronizing signals to the remaining elements of the system requiring them, as illustrated, that is, memories, processors, etc. The signals H (horizontal location), V (vertical location) and SN (depth location) cause the scanning of camera 23 such that when an in focus point or image is detected the value of H, V and SN in digitized form at that instant is stored in the appropriate memories to provide information on the location of the in focus point or image. The video from camera 23 is in analog form and is digitized by an analog to digital converter 25. The digital video LV is distributed to system elements requiring it. The scanning for the embodiment being described is such that for each "SN" a complete frame is scanned from the array. As the focus surface moves forward to the next SN, a continuous process, another complete frame is scanned. Therefore, the time required to capture a complete image or surface, in the volume memory, is the frame scan time times SN. The frame scan time being the time to scan a horizontal line times the number of horizontal lines.

The focusing method is to monitor the high frequency content (amplitude and color variance) of the video at each location of a horizontal line and select the SN where the high frequency content is greatest, and store that portion of the horizontal line at that SN, compensating for curvature of the focused field as previously described.

When an image is out of focus its spacial frequency is low relative to its spacial frequency (or amplitude and color variance) when it is in focus. Making this measurement on a horizontal line provides a reasonable estimate of the degree of focus at a given depth in the scene.

A more precise method would be to "fill" the entire volume memory with imaged pixels and around each pixel select a volume of pixels. We can then measure the variances in multiple directions to characterize the degree of focus in different directions. Also, to compare this situation with the same volumes of pixels at the same pixel (array) location, but at different SN's. Thus, we can characterize the depth of greatest focus as well as the surface slopes at the focused pixel. This approach, although more accurate, appears hardware and processing time-intensive relative to the effective method of using horizontal only, as described below.

Referring again to FIG. 9 the analog video is provided to a high pass filter 26 which measures the color variation (CIE color phase) and the amplitude variation (frequency) and provides these signals to a focus detector 27 which generates a signal related to the magnitude of the two. This signal is digitized in an analog to digital converter 28.

A signal from the focus level memory 29 is provided to a comparator 30 after being converted to analog by digital to analog converter 31. Comparator 30 compares the present focus level to the prior focus level at the same pixel location in the frame. It should be noted that the signal referred to corresponds to a level stored digitally from a prior frame (SN) at the same array location (H and V).

If the present location has a higher focus level AND gate 32 is enabled to allow the live digital video LV to be entered into the focused video memory 33 along with the scene number, SN, yielding an improved estimate in depth, of the depth of the present pixel. Simultaneously, AND gate 34 enables the new selected focus level from converter 31 to be entered into focus level memory 29, replacing the old level. If the present focus level is less than the stored level at that location nothing happens, that is, AND gates 33 and 34 are disabled.

This process repeats continuously, maintaining the focused video memory 33 full of focused data (luminance and chromenence) identified in depth by "SN", and the array location by H and V. Thus, a full focused image is continuously available to the image processor 35 to process and select images.

The above operating mode is when the endoscope is still and no motion is occurring. When the endoscope is moved the scene changes and a new image must be rapidly generated. The detection of motion is accomplished by the use of a low resolution memory which stores the entire surface in a volume memory motion detector memory 36 and a motion detector 37 including comparator logic which compares the incoming video with the low resolution stored image in memory 36. An embodiment for motion detector 37 is disclosed in U.S. Pat. No. 3,988,533.

The low resolution image of memory 36 is compared with the live video LV in motion detector 37 at every location in the memory 36. When significant differences exist then motion is occurring. OR gate 38 and AND gate 32 allows the new video to enter focused video memory 33. When high degrees of motion are present and large areas of the focus video memory 33 have been updated, motion detector memory 36 must also be updated in those regions at a minimum for all "SN's". This is accomplished by AND gate 39 and update circuit 40. Memory 36 being a volume storage memory, could also be used for focus "verification" even though its resolution is lower than the resolution of memory 33.

The ability to selectively add areas of video to the focused video memory 33 is important where motion was detected since situations exist during operating procedures where the instruments represent a small percentage of the field of view and the camera's view of the anatomy is stable. However, instruments move, therefore "motion" occurs where the instruments were and through their path of motion up to their final position. Conversely, the instruments can remain fixed in the field of view of the camera, but the anatomy moves. In the latter case, movement can occur by relocation of the trocar.

The image processor 35 has access to the memory 33 and it calculates actual scene depth from memory 33 (H, V and SN) using the volume focus depth memory 41. This contains the radial line which is rotated to generate the focus surface for all SN's. The depth calculator 42 determines the Δ SN and adds it to SN to provide the actual depth. Due to the discrete numbers of values and symmetry, look up tables can be pipelined and used to avoid computations.

Image processor 35 performs all the major image processing functions required for the trigonometric image manipulation and viewpoint selection. This processing can be color or black or white. Image processor 35 receives slice data from existing tomographic techniques as shown at 43 and processes the slice date and data from the optics head to provide a composite image as described above. Image processor 35 also interfaces with input/output control unit 44 allowing interactive image selection and enhancement. Control unit 44 may be voice commands or joy stick operating as described above. Image processor 34 provides 3-D images to display system 45 which can be a monitor in the simplest form. Generally, the images from processor 34 will be full color containing the viewpoint perspective information. Fields of view will be contained at a far greater level than the present camera view. They will have been previously stored and identified in location within the body cavity. Also, there will be contained some concatenated scenes from camera imagery and from "slice" information which has been volumetrically "spliced" into the imagery both in structure and color.

Figure 10:
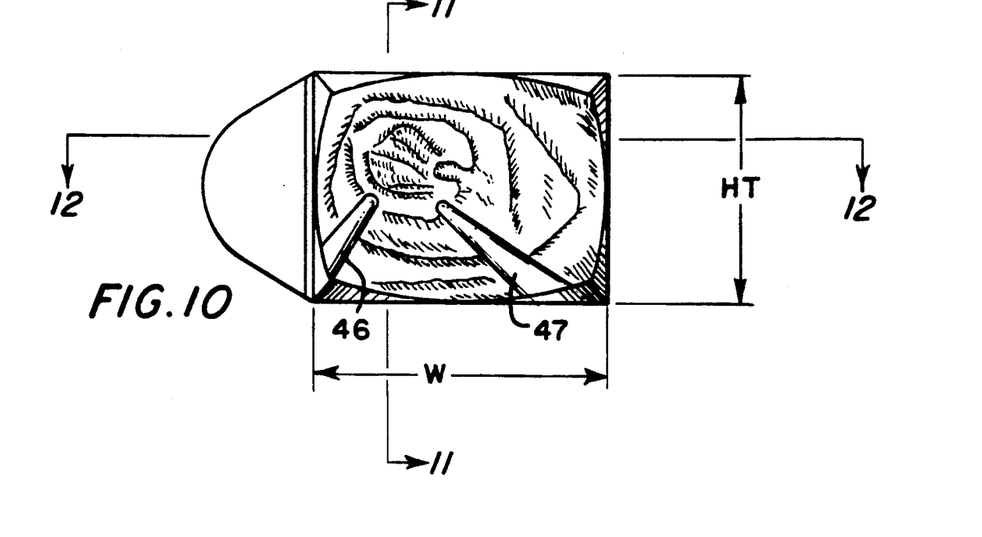
FIG. 10 is a camera view of a body cavity with two instruments in the field of view.
Figure 11:
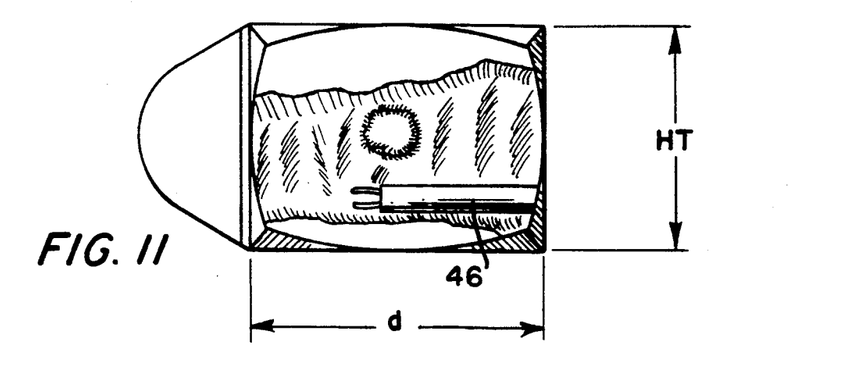
FIG. 11 is a camera view of the body cavity of FIG. 10 taken along line 11—11 of FIG. 10.
Figure 12:
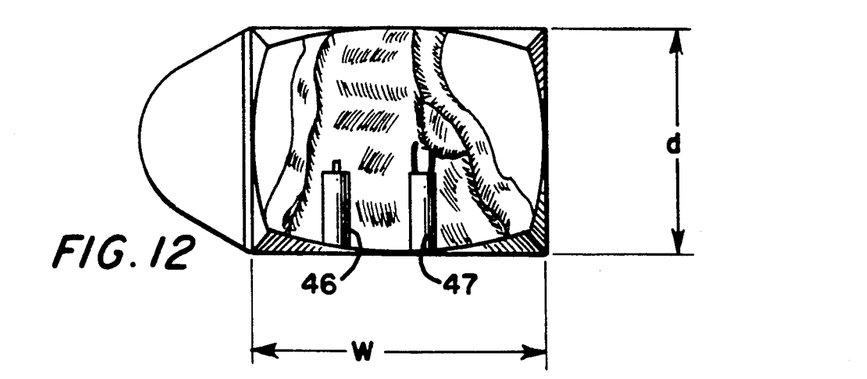
FIG. 12 is a camera view of the body cavity of FIG. 10 taken along line 12—12 of FIG. 10.

FIG. 10 illustrates a camera view of a body cavity having a height HT and a width W with two instruments 46 and 47 in the field of view, and all pixels identified in terms of depth. A horizontal cutting plane along line 11—11 is indicated along with a vertical cutting plane along line 12—12. FIG. 10 shows the camera perspective indicated by the two instruments pointing at a common point.

FIG. 11 illustrates the image obtained after removal of the camera's perspective and viewing without perspective along the vertical cutting plane indicated by line 11—11 of FIG. 10. FIG. 11 has the height HT and the in focus depth d. FIG. 12 is a scene through the cutting plane indicated by line 12—12 of FIG. 10 looking in from the top, without perspective illustrating the width W and depth d.

Clearly, the cutting planes can be located arbitrarily in angle and location. The resulting view from a cutting plane can have perspective added to it since the depth of all pixels from the cutting plane (perpendicular) are known. However, computations would be required to determine them.

Similarly, three dimensional perspectives can be generated as previously described, which allows the viewer to assume any vantage point within the imagery, as well as a "size", relative to the anatomy being viewed.

Figure 13:
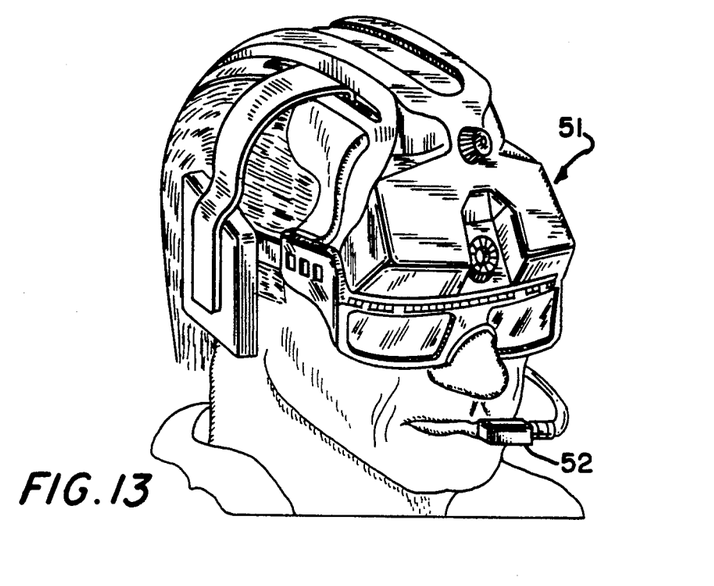
FIG. 13 is a perspective view of a goggle display system that can be employed with the system of FIG. 9.

FIG. 13 shows projection goggles 51 being worn by the surgeon which replaces or is in addition to the display system in the form of a CRT monitor mentioned in conjunction with the description of FIG. 9. The goggles have the dual effect of isolating him/her from the physical surroundings, that is, losing the size and dimensional characteristics of the real world, and allowing him/her to be immersed in the subject anatomy.

The goggle optics can be generated from miniature color CRT's coupled with coherent fiber optic bundles having conventional devices (LCD) to project the images into the eyes. Alternatively, use could be made of coherent tricolor primaries for each image, mechanically scanned into the eyes using holographic optical elements (HOE) to form the image. The surgeon can select desired three-dimensional images by the use of a voice actuated image selector 52.

Clearly the moving lens optics head performs two functions for the system by; (1) allowing a fully focused image to be generated, and (2) allowing precise distance measurements to be made to the surface being imaged.

Alternative embodiments can be provided that allow similar performance characteristics to be achieved.

Figure 14:
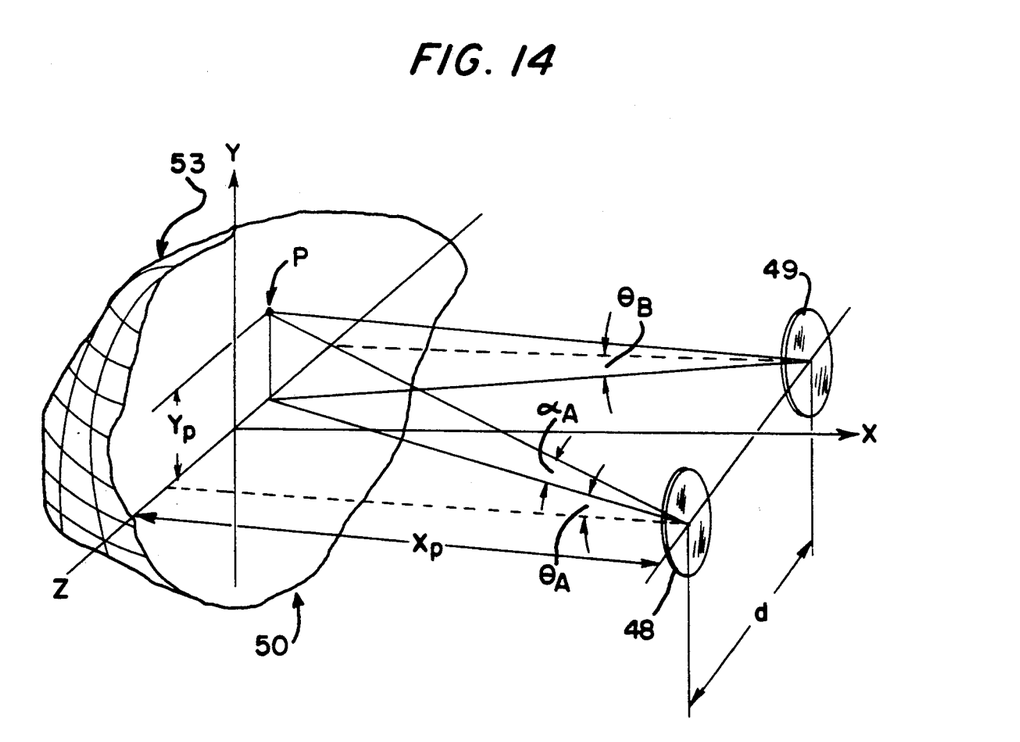
FIG. 14 is a perspective view of a representation of another embodiment of an optics head employed in the imaging system in accordance with the principles of the present invention.

For example, FIG. 14 illustrates a case where two coplanar lenses 48 and 49 are looking into a region 50 containing a surface 53, with one particular point (Pixel) P being considered.

The location of point P in space $(x_p, y_p)$ can be seen to be;

$$x_p = \frac{d}{\TAN \theta_A + \TAN \theta_B}$$

$$y_p = \frac{d \TAN \alpha_A}{\COS \theta_A (\TAN \theta_A + \TAN \theta_B)}$$

The angles being determined from each image of the point. This allows all points on the surface to be defined in space in the same manner. Therefore, the image pixels are all identified in terms of three dimensional locations within the cavity. The lenses 48 and 49 require a large depth of field to maintain focus.

It can be further noted that the requirement for the lenses being coplanar is not required, and only that a relationship identifying their relative positions in space be known as well as their optical characteristics, and that the points being analyzed fall in their "common" field of view.

The above allows a single trocar to carry two lenses into a body cavity, that are in close proximity, or the lenses can be separated, each being entered through separate locations into the common body cavity.

Another example of determining the distance to a focused point, without moving lenses, is the following.

In a situation where an image is defocussed the lens has caused the image of an object point to spread or blur. The resulting image is the linear spacial summation of all of the individual "blurred" points.

If an object light (intensity) distribution can be represented by; $f(x_o,y_o)$ and an image distribution from $f(x_o,y_o)$ caused by a lens with a point spread function (PSF) $h\{|x_oy_ox_iy_i|^2\}$ can be represented by; $g(x_i,y_i)$ then the relationship governing the image formation is;

$$g(x_i, y_i) = \int_{-\infty}^{+\infty} \int_{-\infty}^{+\infty} f(x_0, y_0) h\{|x_0, y_0, x_i, y_i|^2\} dx_0 dy_0$$

for incoherent (broad band) light, and no magnification.

If the effect of the PSF is uniform across the object and image (i.e. spacially invariant) the image can be represented by;

$$g(x_i, y_i) = \int_{-\infty}^{+\infty} \int_{-\infty}^{+\infty} f(x_0, y_0) h|(x_i - x_0),(y_i - y_0)|^2 dx_0 dy_0$$

If the PSF is not uniform throughout the image field, regions can be selected where it is approximately uniform, (isoplanatic patches) and PSF's can be determined for each region.

The above relationship, being a spacial convolution, can also be represented in the frequency domain by the product of the Fourier transforms of the object distribution and the PSF, $$G_i(W_x, W_y) = F_o(W_x, W_y) H[W_x, W_y]$$

For a single lens of fixed focal length, and free of distortions, the image will be in focus when the object distance is such that;

$$d_0 = \frac{fd_i}{d_i - f}$$

$d_0$ = object dist.

$d_i$ = image dist.

$f$ = focal length

At all other distances blurring will occur, and to a degree that is directly related to the distance the object differs from $d_o$.

Due to field curvature the object surface that causes a non blurred image could be shaped parabolically as in FIG. 4, and with radial symmetry.

Since the optical system is known in terms of its optical characteristics, the PSF (optical transfer function (OTF) in the frequency domain) can be measured at various degrees of defocus by computing;

$$H_d[W_x, W_y] = \frac{G_i[W_x, W_y]}{F_0[W_x, W_y]}\bigg|_{d=const}$$

These computed values of $H_d(W_x,W_y)$ which are "object" or "scene" independent, but are dependent on "d" the distance to the object, and most likely the distance radially to the object from the optical axis, can be used to restore the image from its blurred state. By using its inverse to filter the blurred image the original image can be restored or deblurred. This can be achieved with digital or optical computers.

For example, the blurred image resulted from the convolution of the PSF (that occurs when the object is a distance d from the lens) with the original image.

$$G(W_x, W_y) = F(W_x, W_y) H(W_x, W_y)_d$$

The original image can be restored by using the inverse of the OTF on the blurred image $$F(W_x, W_y) = G_d(W_x, W_y)[H(W_x, W_y)_d]^{-1}$$

$G_d(W_x,W_y)$ being the image from the camera, which was blurred due to the object being a distance d from the lens. $H[(W_x,W_y)_d]^{-1}$ is the inverse of the OTF measured from the system optics when the object was a distance d from the lens.

When looking into a three dimensional cavity, the image from the camera contains all of the surface information with different degrees of blur in different areas depending on the distance of the objects on the surface from the lens. By sequentially selecting the "stored" $H_d[W_x,W_y]i$ for different distances, and generating a series of images that are deblurred for different surface to lens distances, by "deconvolving" them with the image, a series of images result that simulate the images captured by the moving lenses of FIGS. 1, 3 and 4.

By using this series of images as if they were from the moving lenses and providing them to the focus detection circuitry of the system of FIG. 9, the same process will allow the focused video memory to be filled with "focused pixels".

From a system viewpoint the exact inverse of $H(W_x,W_y)$ may need further conditioning do to singularities in its structure (i.e. division by 0). Techniques using matrix filtering and manipulation have been devised to ease this problem, such as disclosed in "Digital Image Restoration" H. C. Andrews, 1977, Prentice-Hall ISBN 0-13-214 213-9.

While we have described above the principles of our invention in connection with specific apparatus, it is to be clearly understood that this description is made only by way of example and not as a limitation to the scope of our invention as set forth in the objects thereof and in the accompanying claims.

I claim:

1. A method of providing images of internal anatomy of a mammal comprising the steps of
    generating externally of said mammal tomographic slice data by existing tomography techniques;
    providing from said slice data first images of a selected one of body cavities of said mammal;
    producing internally of said mammal second images of said selected one of said body cavities; and
    correlating said first and second images to generate composite images of said selected one of said body cavities in real time, in large fields of view and in three-dimensions.

2. A method according to claim 1, wherein said step of producing includes the step of
obtaining a plurality of different in focus images of the interior of said selected one of said body cavities as said second images.

3. A method according to claim 1, further including the step of
utilizing said first images to externally select a path through said selected one of said body cavities from a given point on the epidermis of said mammal to a surgical site in said selected one of said body cavities.

4. A method according to claim 3, wherein said step of producing includes the step of obtaining a plurality of different in focus images of the interior of said selected one of said body cavities as said second images.

5. A method according to claim 3, further including the step of
selecting predetermined three-dimensional views from said composite images for viewing on a display system.

6. A method according to claim 5, wherein said step of producing includes the step of
obtaining a plurality of different in focus images of the interior of said selected one of said body cavities as said second images.

7. A method according to claim 1, further including the step of
selecting predetermined three-dimensional views from said composite images for viewing on a display system.

8. A method according to claim 7, wherein said step of producing includes the step of
obtaining a plurality of different in focus images of the interior of said selected one of said body cavities as said second images.

9. A system to provide images of internal anatomy of a mammal comprising:
first means to externally generate tomographic slice data by existing tomographic techniques to provide first images of a selected one of body cavities of said mammal;
second means for disposal internally of said mammal to produce second images of said selected one of said body cavities; and
third means coupled to said first means and said second means to correlate said first and second images to generate composite images of said selected one of said body cavities in real time, in large fields of view and in three-dimensions.

10. A system according to claim 9, wherein said second means includes
optical means to provide a plurality of different in focus images of the interior of said selected one of said body cavities as said second images.

11. A system according to claim 10, wherein said optical means includes
a plurality of lenses disposed in a tandem relationship along a common optical axis providing at a given distance from said plurality of lenses in said selected one of said body cavities certain ones of said plurality of different in focus images, and
fourth means coupled to said plurality of lenses to move said plurality of lenses relative to each other to enable adjustment of said given distance to enable obtaining others of said plurality of different in focus images.

12. A system according to claim 10, wherein said optical means includes
at least a pair of lenses disposed in a side-by-side spaced relation with respect to each other looking into said selected on of said body cavities, said pair of lenses providing said plurality of different in focus images in a field of view common to said pair of lenses.

13. A system according to claim 9, further including fourth means coupled to said first means to enable a surgeon to manipulate said first images to externally select a path through said selected one of said body cavities from a given point on the epidermis of said mammal to a surgical site in said selected one of said body cavities.

14. A system according to claim 13, wherein said second means includes
optical means to provide a plurality of different in focus images of the interior of said selected one of said body cavities as said second images.

15. A system according to claim 14, wherein said optical means includes
a plurality of lenses disposed in a tandem relationship along a common optical axis providing at a given distance distance from said plurality of lenses in said selected one of said body cavities certain ones of said plurality of different in focus images, and
fifth means coupled to said plurality of lenses to move said plurality of lenses to move said plurality of lenses relative to each other to enable adjustment of said given distance to enable obtaining others of said plurality of different in focus images.

16. A system according to claim 14, wherein said optical means includes
at least a pair of lenses disposed in a side-by-side spaced relation with respect to each other looking into said selected one of said body cavities, said pair of lenses providing said plurality of different in focus images in a field of view common to said pair of lenses.

17. A system according to claim 13, further including fifth means coupled to said third means to enable said surgeon to select predetermined three-dimensional views from said composite images for viewing on said display system.
a display system; and 18. A system according to claim 17, wherein said second means includes
optical means to provide a plurality of different in focus images of the interior of said selected one of said body cavities as said second images.

19. A system according to claim 18, wherein said optical means includes
a plurality of lenses disposed in a tandem relationship along a common optical axis providing at a given distance from said plurality of lenses in said selected one of said body cavities certain ones of said plurality of different in focus images, and
sixth means coupled to said plurality of lenses to move said plurality of lenses relative to each other to enable adjustment of said given distance to enable obtaining others of said plurality of different in focus images.

20. A system according to claim 18, wherein said optical means includes at least a pair of lenses disposed in a side-by-side spaced relation with respect to each other locking into said selected one of said body cavities said pair of lenses providing said plurality of different in focus images in a field of view common to said pair of lenses.

21. A system according to claim 9, further including a display system; and fourth means coupled to said third means to enable a surgeon to select predetermined three-dimensional views from said composite images for viewing on said display system.

22. A system according to claim 21, wherein said second means includes optical means to provide a plurality of different in focus images of the interior of said selected one of said body cavities as said second images.

23. A system according to claim 22, wherein said optical means includes a plurality of lenses disposed in a tandem relationship along a common optical along a common optical axis providing at a given distance from said plurality of lenses in said selected one of said body cavities certain ones of said plurality of different in focus images, and fifth means coupled to said plurality of lenses to move said plurality of lenses relative to each other to enable adjustment of said given distance to enable obtaining others of said plurality of different in focus images.

24. A system according to claim 22, wherein said optical means includes at least a pair of lenses disposed in a side-by-side spaced relation with respect to each other looking into said selected one of said body cavities said pair of lenses providing said plurality of different in focus images in a field of view common to said pair of lenses.

* * * * *